United States Patent
Getman et al.

(10) Patent No.: US 6,263,731 B1
(45) Date of Patent: Jul. 24, 2001

(54) METHOD AND ASSEMBLY FOR MONITORING A PREDETERMINED LEVEL IN A CONTAINER

(75) Inventors: Igor Getman; Sergej Lopatin, both of Lörrach (DE)

(73) Assignee: Endress + Hauser GmbH + Co., Maulburg (DE)

( * ) Notice: Subject to any disclaimer, the term of this patent is extended or adjusted under 35 U.S.C. 154(b) by 0 days.

(21) Appl. No.: 09/067,129

(22) Filed: Apr. 27, 1998

(30) Foreign Application Priority Data

May 5, 1997 (DE) .............................. 197 18 965

(51) Int. Cl.⁷ ............................ G01F 23/28; G08B 21/00
(52) U.S. Cl. ..................................... 73/290 V; 73/861.27; 340/620; 340/621; 367/908
(58) Field of Search ................... 73/290 V, 291, 73/861.27, 1.83, 610, 612, 626, 628; 340/621, 620; 310/317; 367/908

(56) References Cited

U.S. PATENT DOCUMENTS

| | | |
|---|---|---|
| 3,748,635 | 7/1973 | Phillips et al. ................... 373/13 |
| 4,299,114 | 11/1981 | Silvermetz et al. ............... 73/1.83 |
| 4,336,719 | * 6/1982 | Lynnworth ..................... 73/861.27 |
| 4,596,144 | * 6/1986 | Panton et al. .................. 73/290 V |
| 4,610,164 | 9/1986 | Sobue et al. ................... 73/290 V |
| 5,155,472 | * 10/1992 | Dam ............................ 73/290 V |
| 5,269,188 | 12/1993 | Esin et al. ...................... 73/610 |
| 5,319,972 | * 6/1994 | Oblak et al. ................... 73/290 R |
| 5,437,178 | * 8/1995 | Esin et al. ..................... 73/290 V |
| 5,644,299 | 7/1997 | Cruickshank ................... 340/617 |
| 5,697,248 | * 12/1997 | Brown .......................... 73/290 V |
| 5,836,192 | * 11/1998 | Getman et al. ................. 73/290 V |
| 5,983,730 | * 11/1999 | Freund et al. ................. 73/861.27 |

FOREIGN PATENT DOCUMENTS

| | | |
|---|---|---|
| 30 05 851 | 9/1981 | (DE) . |
| 195 20 516 | 12/1995 | (DE) . |
| 195 38 678 | 4/1997 | (DE) . |

* cited by examiner

Primary Examiner—Hezron Williams
Assistant Examiner—Michael Cygan
(74) Attorney, Agent, or Firm—Bose McKinney & Evans LLP

(57) ABSTRACT

An assembly for monitoring a predetermined level of a material in a container comprises two ultrasonic transducers mounted on the container in line with the level to be monitored, such that an interspace exists between the ultrasonic transducers into which the material enters on attaining the level to be monitored. The one ultrasonic transducer is an emitter transducer which at predetermined points in time for emitting ultrasonic pulses is energized by a frequency which is so low that the ultrasonic pulses are transmitted through the interspace to the detector transducer even when the interspace is filled with air. The other ultrasonic transducer is a detector transducer which converts detected ultrasonic pulses into electrical detection signals. To determine whether or not material is in the interspace between the ultrasonic transducers a check is made as to whether the detector transducer outputs after each point in time of emission a detection signal in a time interval corresponding to the transit time of the ultrasonic pulses from the emitter transducer to the detector transducer in air.

27 Claims, 3 Drawing Sheets

METHOD AND ASSEMBLY FOR MONITORING A PREDETERMINED LEVEL IN A CONTAINER

Figure 1:
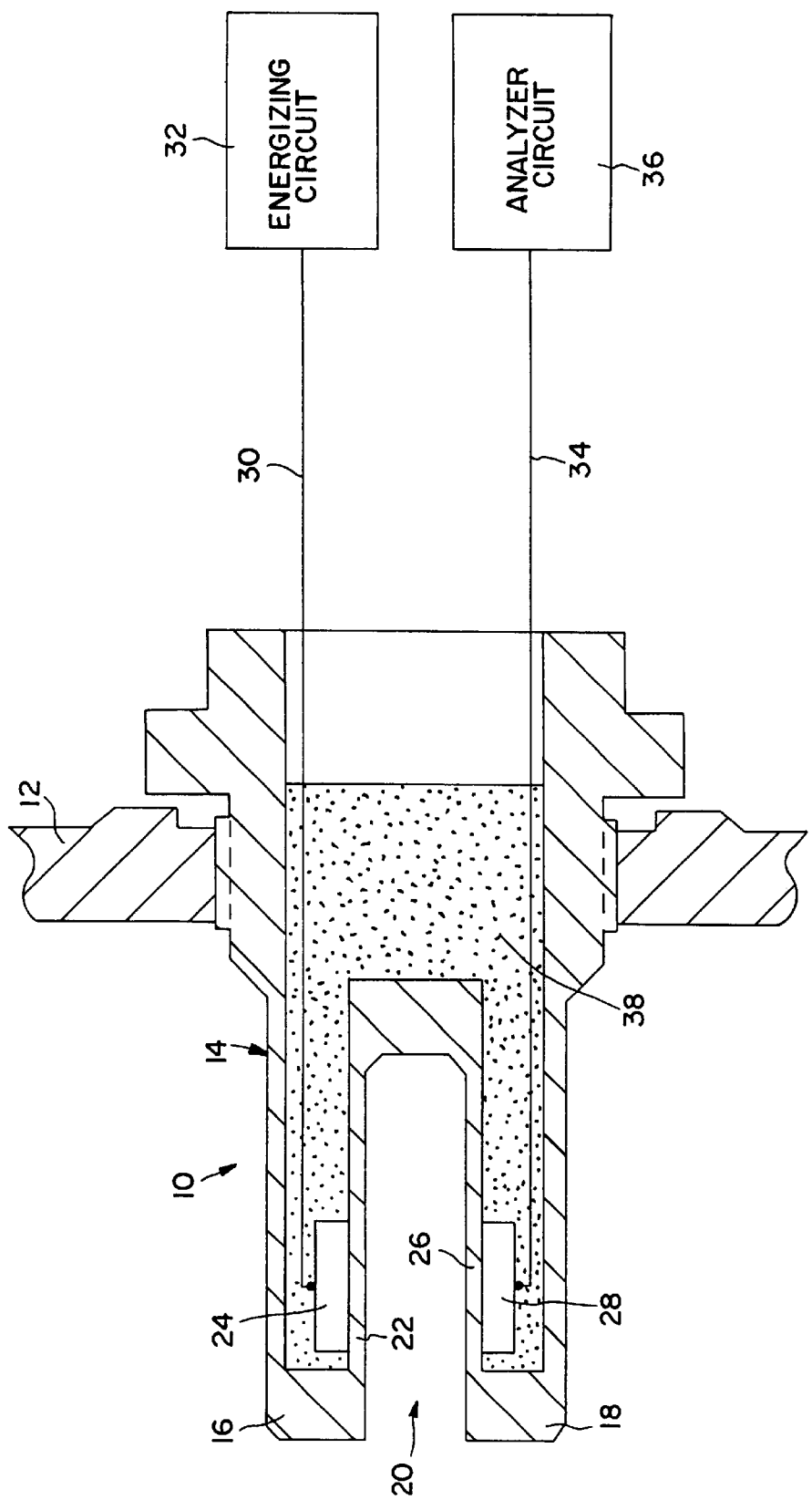

The invention relates to a method for monitoring a predetermined level of a material in a container with the aid of two ultrasonic transducers mounted on the container in line with the level to be monitored such that an interspace exists between the ultrasonic transducers into which the material enters on attaining the level to be monitored, whereby the one ultrasonic transducer is an emitter transducer energized at predetermined points in time to emit ultrasonic pulses into the interspace whilst the other ultrasonic transducer is a detector transducer which converts the detected ultrasonic pulses into electrical detection signals, the analysis of which indicates whether material is in the interspace between the ultrasonic transducers. The invention relates further to an assembly for implementing the method.

In a related method known from U.S. Pat. No. 5,269,188 it is sensed whether the detector transducer outputs a detection signal after the point in time of emission corresponding to the transit time for ultrasonic pulses to pass through a liquid contained in the interspace between the sensors. For this purpose a main time window is formed in which the detection signal is required to appear for each speed of sound materializing in the liquid. In addition a test time window is formed ahead of the main time window in which a detection signal appears when the detector transducer detects an ultrasonic pulse which has been transmitted through the support of the two transducers from the emitter transducer to the detector transducer. This test is based on the speed of sound in the solid material comprising the support being greater than the speed of sound in the liquid. The existence or lack of a detection signal in the main time window with a detection signal simultaneously present in the test time window is used as a criterion of whether or not liquid exists in the interspace. If instead of liquid, air is in the interspace then it is assumed that no ultrasonic pulse has passed through the interspace to the detector transducer; this also being true at the high ultrasonic frequencies typically employed.

In the case of the related methods known from other publications (WO 82/04122; GB Patent 1,578,031; U.S. Pat. No. 4,630,245) the criterion of the interspace between the ultrasonic transducers being filled with a liquid or not is taken to be whether ultrasonic pulses arrive at the detector transducer at a time following each point in time of emission corresponding to the transit time for the ultrasonic pulses through the liquid.

Application of these known methods is thus restricted to monitoring the level of liquids having corresponding ultrasonic transmission properties, i.e. difficulties may arise, for example, when the liquid to be monitored is heavily aerated. Furthermore, no materials can be monitored by these known methods which fail to transmit ultrasonic waves, this applying more particularly to bulk (powdery or fine-grain) material such as meal, sand or the like.

The object of the invention is to define a method of the aforementioned kind which permits monitoring the level irrespective of the ultrasonic transmission properties of the material concerned.

In accordance with the invention this object is achieved in that the emitter transducer emitting the ultrasonic pulses is activated at a frequency which is so low that the ultrasonic pulses are transmitted through the interspace to the detector transducer even when the interspace is filled with air and that it is determined whether the detector transducer outputs after each point in time of emission a detection signal in an interval corresponding to the transit time of the ultrasonic pulses from the emitter transducer to the detector transducer in air.

In the method in accordance with the invention the arrival of ultrasonic pulses transmitted through the air in the interspace is taken as a criterion as to whether the interspace is filled with air or the material being monitored. This is possible when the frequency of the ultrasonic waves is sufficiently low, preferably smaller than approximately 300 kHz since ultrasonic waves of such a low frequency are still transmitted with sufficient amplitude even through air. The ultrasonic pulses transmitted through air can be explicitly distinguished from the ultrasonic pulses transmitted through a liquid due to their longer transit time, they permitting monitoring the level even then when the material to be monitored does not transmit ultrasonic waves, i.e. in the case of powdery or fine-grain solids, for example.

When the material is a liquid an advantageous further aspect of the method in accordance with the invention enables it to be additionally determined whether the detector transducer outputs after a point in time of emission a detection signal in a time interval corresponding to the transit time of the ultrasonic pulses from the emitter transducer to the detector transducer in the liquid, as a result of which high accuracy is attained because a detection signal indicating the existing condition needs to exist in each emission cycle in both the empty and filled condition of the interspace.

When, by contrast, the material has such a consistency that it does not transmit ultrasonic waves the accuracy can be enhanced by additionally establishing whether the detector transducer outputs a detection signal after each point in time of emission in a time interval corresponding to the transit time of the ultrasonic pulses from the emitter transducer to the detector transducer through the support of the two transducers.

An assembly for implementing the method in accordance with the invention comprising two ultrasonic transducers mounted on the container in line with the level to be monitored, such that an interspace exists between the ultrasonic transducers into which the material enters on attaining the level to be monitored, whereby the one ultrasonic transducer is an emitter transducer configured and arranged so that on being energized by an electrical alternating voltage pulse it emits ultrasonic pulses into the interspace whilst the other ultrasonic transducer is a detector transducer configured and arranged so that it converts the detected ultrasonic pulses into electrical detection signals, including an energizing circuit to energize the emitter transducer at predetermined points in time of emission to emit ultrasonic pulses, and an analyzer circuit for analyzing the electrical detection signals furnished by the detector transducer to determine whether the interspace is filled with the material to be monitored or not is characterized in accordance with the invention by the energizing circuit energizing the emitter transducer for emitting ultrasonic pulses at a frequency which is so low that they are transmitted through the interspace to the detector transducer even when the interspace is filled with air and by the analyzer circuit containing a means to distinguish whether the detector transducer outputs after each point in time of emission a detection signal in a time interval corresponding to the transit time of the ultrasonic pulses from the emitter transducer to the detector transducer in air.

In one advantageous aspect of this assembly the two ultrasonic transducers are piezoelectric transducers made of a porous piezoelectric ceramic having a connectivity of 3—3. Such relatively compact ultrasonic transducers are able to operate in the necessary low-frequency ultrasonic frequency range of approximately 100 to 300 kHz without requiring furthermore an adapter film.

Figure 2:
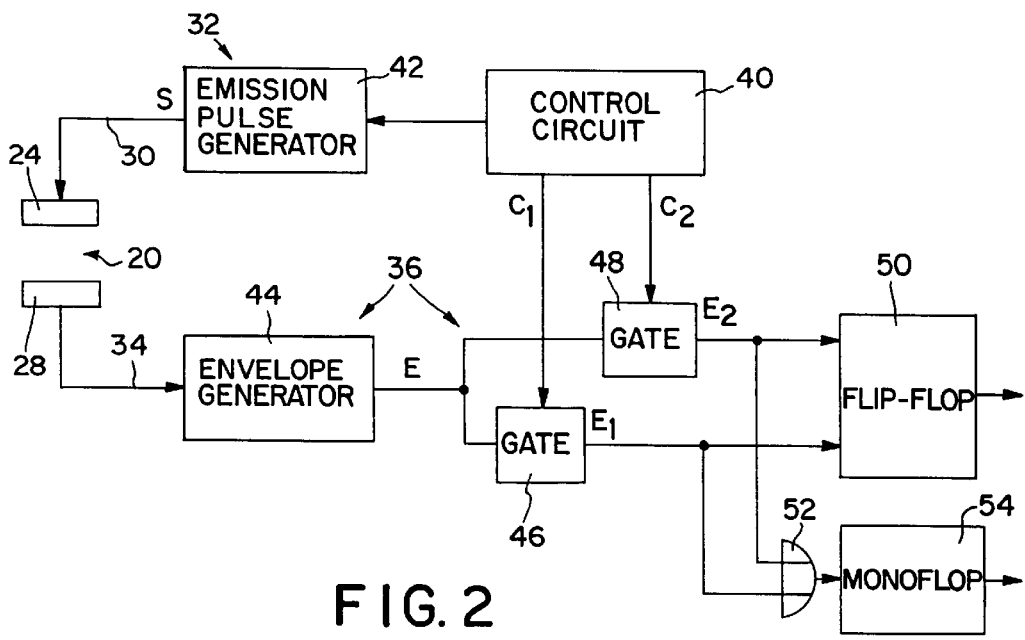
Figure 3:
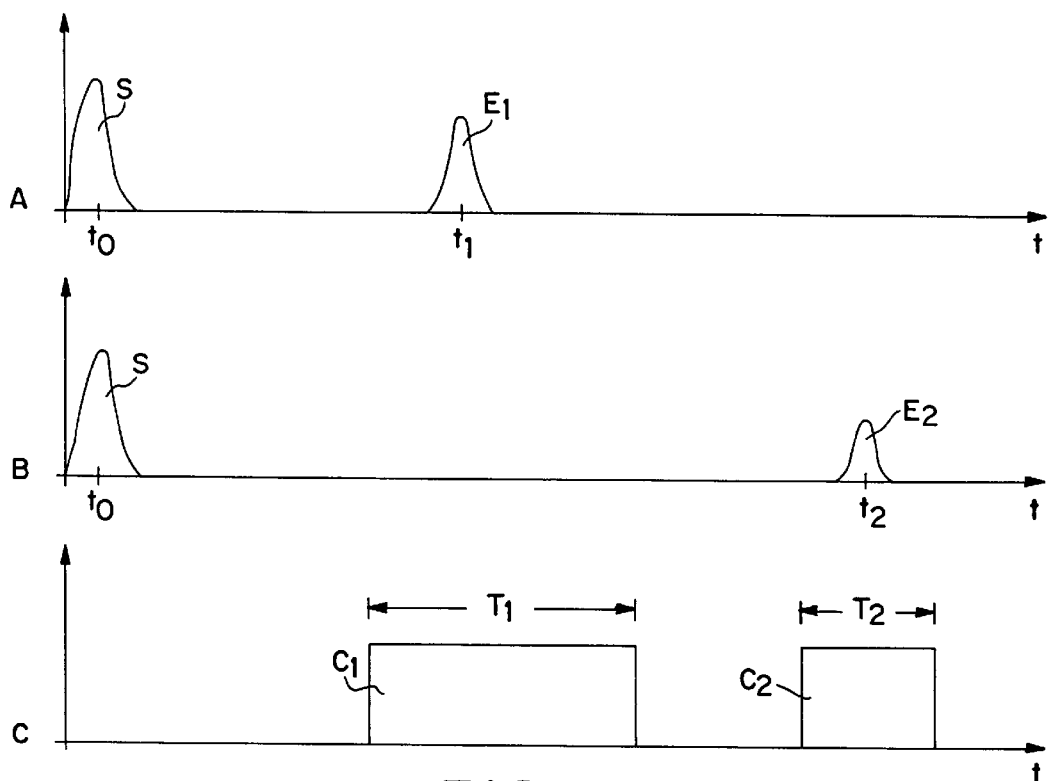
Figure 4:
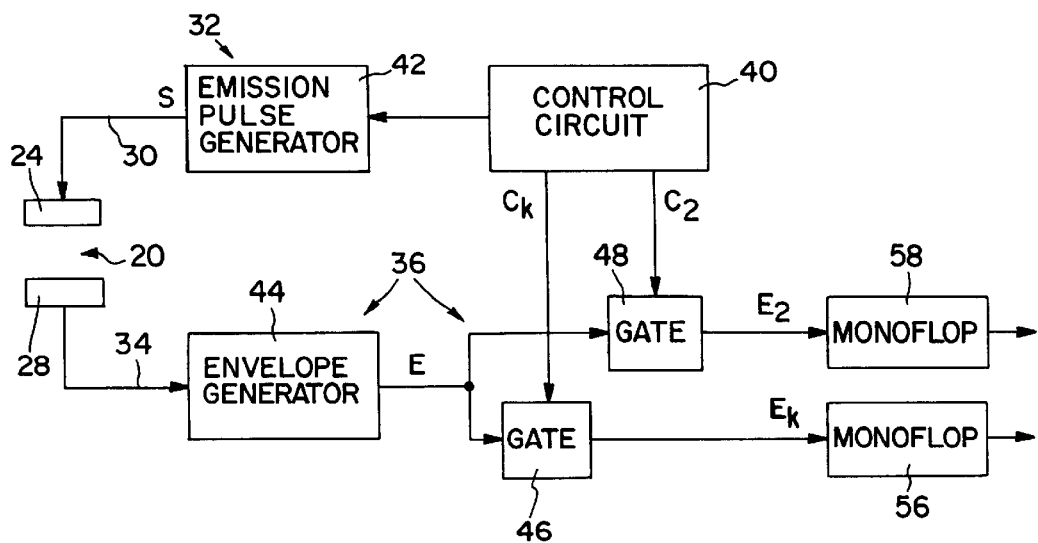
Figure 5:
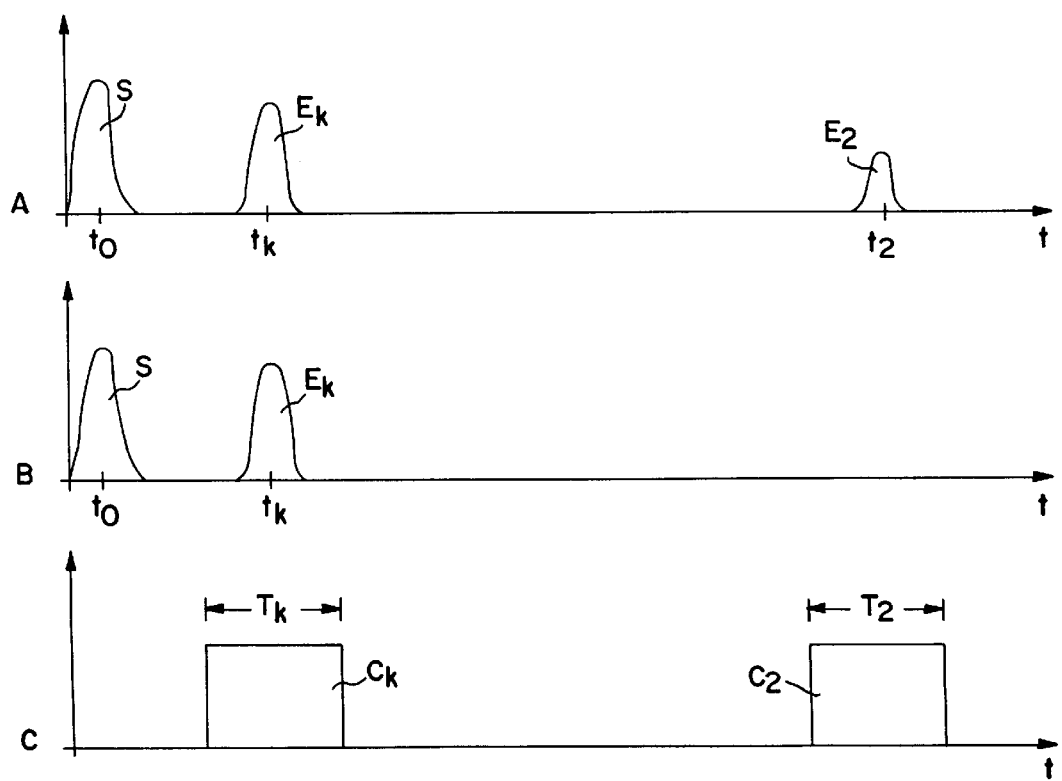

Further features and advantages of the invention read from the following description of example embodiments with reference to the drawing in which:

FIG. 1 illustrates an assembly for monitoring a predetermined level in a container in accordance with the invention, FIG. 2 is the block diagram of one embodiment of the energizing circuit and the analyzer circuit of the assembly as shown in FIG. 1 when the material to be monitored is a liquid, FIG. 3 shows time plots explaining how the assembly as shown in FIG. 2 functions, FIG. 4 is the block diagram of a modified embodiment of the energizing circuit and the analyzer circuit of the assembly as shown in FIG. 1 and FIG. 5 shows time plots explaining how the assembly as shown in FIG. 4 functions.

Referring now to FIG. 1 there is illustrated an assembly for monitoring a predetermined level of a material in a container comprising a sensor 10 inserted in an opening in the wall 12 of the container so that it protrudes into the interior of the container. The sensor 10 has a housing 14, the portion of which located in the interior of the container forms two parallel housing sections 16, 28 between which an interspace 20 exists. Incorporated in the housing section 16 at the wall 22 adjacent to the interspace 20 is an ultrasonic transducer 24, and incorporated in the housing section 18 at the wall 26 adjacent to the interspace 20 is an ultrasonic transducer 28 so that it is opposite ultrasonic transducer 24. The ultrasonic transducer 24 serves as the emitter transducer and it is connected by a lead 30 to the energizing circuit 32 arranged outside of the container. The ultrasonic transducer 28 serves as the detector transducer and is connected by a lead 34 to the analyzer circuit 36 arranged outside of the container. Incorporated in the interior of the housing 14 is a compound 38 in which the ultrasonic transducers 24, 28 are embedded. The housing 14 serving as the support of the two ultrasonic transducers 24 and 28 may be made of a metal or plastics material.

The sensor 10 is fitted to the container in line with the level to be monitored so that the interspace 20 is filled with the material when the level to be monitored is attained or exceeded whilst the interspace 20 is filled with air when the level to be monitored is not attained.

The energizing circuit 32 generates electrical emission pulses which are applied to the ultrasonic transducer 24. The ultrasonic transducer 24 is energized by each electrical emission pulse causing it to vibrate ultrasonically at the frequency of the electrical emission pulse, and it is configured and arranged so that it emits a pulsed ultrasonic wave having this frequency into the interspace 20. The detector transducer 28 is configured and arranged so that it transduces each ultrasonic pulse arriving from the emitter transducer 24 into an electrical detection signal having the same frequency, this signal being applied to the analyzer circuit 36.

Referring now to to FIG. 2 there is illustrated an example embodiment of the energizing circuit 32 and the analyzer circuit 36 for the case in which the material in the container is a liquid. This Figure shows, again schematically, the emitter transducer 24 and the detector transducer 28 arranged on both sides of the interspace 20. A control circuit 40 controls the sequence of operations in the energizing circuit 32 and in the analyzer circuit 36. The energizing circuit 32 contains an emission pulse generator 42 having a trigger input connected to the control circuit 40 and which is connected to the output of the emitter transducer 24 via a lead 30. The control circuit 40 sends periodic trigger pulses to the emission pulse generator 42 which for each trigger pulse applies an electrical emission pulse S having the frequency of the ultrasonic wave to be emitted to the emitter transducer 24, as a result of which the latter is energized to emit an ultrasonic pulse having this frequency.

As is known, the reach of the ultrasonic waves having a high frequency (approximately 2 MHz) is very limited in air whilst such ultrasonic waves are well able to propagate in liquids. If ultrasonic waves of such a high frequency were to be emitted in the assembly as shown in FIG. 1 the ultrasonic waves emitted by the emitter transducer 24 would only attain the detector transducer 28 if the interspace 20 were filled with a liquid, whereas the detector transducer 29 would detect no ultrasonic pulses if the interspace 20 were filled with air. Likewise, the detector transducer 28 would not detect ultrasonic pulses having such a high frequency if the liquid were aerated.

In accordance with the invention, however, the frequency of the emission pulses generated by the emission pulse generator 42 is so low that the ultrasonic pulses emitted by the emitter transducer 24 and having the same frequency attain the detector transducer 28 even when only air is present in the interspace 20 or the liquid is aerated. The detector transducer 28 thus detects ultrasonic pulses both when the interspace 20 is filled with air and when it is filled with liquid, this then being the case when the frequency of the ultrasonic waves is smaller than approximately 300 kHz. Preferably the frequency of the ultrasonic pulses is in the range of approximately 100 to 300 kHz. At these frequencies the ultrasonic pulses attain the detector transducer 28 through the interspace 20 filled with air with an intensity which is still sufficient when the space between the emitter transducer 24 and the detector transducer 28 is a few centimeters. At a frequency of 200 kHz this space is preferably between 1 cm and 3 cm.

So that the analyzer circuit 36 is able to "see" whether the level to be monitored has been attained use is made of the fact that ultrasonic waves propagate faster in a liquid than in air. The analyzer circuit 36 is thus configured so that it is able to establish from the point in time of arrival of an ultrasonic pulse whether or not the level to be monitored has been attained. This can be achieved for example by the embodiment of the analyzer circuit 36 as shown in FIG. 2.

The ultrasonic pulses arriving at the detector transducer 28 are converted thereby into electrical detection signals which are passed on to the analyzer circuit 36 via the lead 34. The analyzer circuit 36 contains an envelope generator 44 which receives at its input the electrical detection signals arriving from the detector transducer 28 and outputs at its output a signal E representing the envelope of each detection signal. The output of the envelope generator 44 is connected in parallel to the inputs of two gating circuits 46, 48 which are opened and closed by control signals $C_1$ and $C_2$ respectively as furnished by the control circuit 40. The outputs of the two gating circuits 46 and 48 are connected to two inputs of a flip-flop 50 which is transposed by a signal passed on by the gating circuit 46 into the one state and by a signal passed on by the gating circuit 48 into the opposite state. Furthermore, the outputs of the two gating circuits 46 and 48 are connected to the two inputs of an OR circuit 52 at the output of which the input of a retriggerable monoflop 54 is connected.

Referring now to FIG. 3 the functioning of the assembly as described will be explained with reference to the time plots as shown therein. Plot A shows an emission pulse S emitted at the point in time to and the corresponding detection signal $E_1$ output by the detector transducer 28 at the point in time $t_1$ when the interspace 20 is filled with liquid.

Plot B shows again the emission pulse S emitted at the point in time to and the corresponding detection signal $E_2$ output by the detector transducer 28 at the point in time $t_2$ when the interspace 20 is filled with air. The point in time $t_2$ is spaced away further in time behind the point in time to of emission than the point in time $t_1$.

In conclusion plot C in FIG. 3 shows the control signals $C_1$ and $C_2$ which the control circuit 40 applies to the gating circuits 46 and 48 respectively. The control signal $C_1$ opens the gating circuit 46 during a time window $T_1$ in which the point in time $t_1$ is located. The time window $T_1$ is dimensioned large enough so that then when the interspace 20 is filled with liquid the point in time tof arrival of the detection signal $E_1$ is located within the time window $T_1$ for all speeds of sound occurring in the liquid. Changes in the speed of sound in the liquid may be caused by changes in temperature, but also by bubbles forming in the liquid.

Correspondingly, the time window $T_2$ is dimensioned so large than then when the interspace 20 is filled with air the point in time $t_2$ of arrival of the detection signal $E_2$ is located within the time window $T_2$ for all speeds of sound occurring in air. Changes in the speed of sound in air are caused primarily by changes in temperature. The time windows $T_1$ and $T_2$ must not overlap. This requirement can be easily satisfied due to the considerable difference in the speed of sound in liquid on the one hand and in air on the other.

Thus, when a detection signal $E_1$ arrives within the time window $T_1$ it is passed on by the opened gating circuit 46 and it transposes the flip-flop 50 into one of its two states in which its output signal indicates that the interspace 20 is filled with liquid and as a result of which the level to be monitored has been attained or exceeded, whereas when an input signal $E_2$ arrives within the time window $T_2$ it is passed on by the opened gating circuit 48 and it transposes the flip-flop 50 into the other state in which its output signal indicates that the interspace 20 is filled with air and accordingly the level to be monitored has not been attained.

Furthermore each detection signal $E_1$ or $E_2$ passed on by the gating circuits 46 and 48 respectively is applied via the OR circuit 52 to the retriggerable monoflop 54. The holding time of the monoflop 54 is longer than the period of the emission pulses S so that within the holding time at least one detection signal $E_1$ or $E_2$ causes retriggering of the monoflop 54. The monoflop 54 then retains its working state and the output signal of the monoflop 54 indicates that the assembly is working satisfactorily, whereas when no detection signals $E_1$ or $E_2$ arrive within the holding time the monoflop returns to its idle state in which its output signal signifies a faulty condition. Preferably the holding time of the monoflop 54 is a multiple of the emission pulse period so that the fault signal does not occur until the detection signals have been missing in several emission cycles in sequence.

If the material in the container is not a liquid, but a bulk (powdery or fine-grain) solid such as meal, sand or the like the low frequency employed also results in no ultrasonic pulses being transmitted through the interspace 20 when the latter is filled with the solid. One substantial advantage of the method as described is that in this case too, it can be explicitly determined whether the level to be monitored is attained or not. If namely the detector transducer 28 furnishes a detection signal after emission of an ultrasonic pulse in an interval in time corresponding to the transit time of the ultrasonic pulse in air then this means that the interspace 20 is filled with air, i.e. that the level to be monitored has not been attained, whereas if the detector transducer 28 furnishes no detection signal after the point in time of emission in this interval in time then this means that the interspace 20 is not filled with air and thus the level to be monitored has been attained or exceeded.

So that a decision can be made in this case whether the arrival of a detector transducer is missing due to the level to be monitored having been attained or due to a fault condition an additional fault check needs to be made. This fault check too, can be done by establishing the point in time of arrival of the detection signals when the support of the ultrasonic transducers is configured so that the ultrasonic pulses generated by the emitter transducer 24 gain access to the detector transducer 28 directly through the support. This is the case, for example, in the example embodiment of the sensor 10 as shown in FIG. 1 in which the ultrasonic pulses are transmitted from the emitter transducer 24 to the detector transducer 28 not only through the air gap 20 but also through the walls 22 and 26 of the housing 14 which is made of a metal or plastics material and forms the support of the ultrasonic transducers. In the configuration of the housing shown in FIG. 1 these ultrasonic pulses arrive—despite the somewhat longer path—at the detector transducer 28 earlier than ultrasonic pulses transmitted through air in the interspace 20 because the speed of sound in a metal or plastics material is considerably higher than the speed of sound in air.

Monitoring a predetermined level of a bulk solid can thus be done with the sensor 10 as shown in FIG. 1 without any design modification; all that is required is a minor modification to the analyzer circuit 36. FIG. 4 illustrates an example embodiment of the analyzer circuit 36 making this monitoring possible.

Referring now to to FIG. 4 there are illustrated circuit components corresponding to those of the example embodiment as shown in FIG. 2, they being identified by the same reference numerals as therein; these circuit components thus require no repeat explanation. The differences as compared to the example embodiment as shown in FIG. 2 are merely as follows:

connected to the output of each gating circuit 46 and 48 is a retriggerable monostable multivibrator 56 and 58 respectively, the holding time of which is longer than the period of the emission pulses S;

the gating circuit 56 is opened by a control signal $C_k$ from the control circuit 40 for the duration of a time window in which an emission pulse transmitted through the housing 14 arrives at the detector transducer 28.

Referring now to to FIG. 5 the functioning of the assembly incorporating the analyzer circuit as shown in FIG. 4 will be explained with reference to the time plots as shown in FIG. 5. Plot A shows an emission pulse S emitted at the point in time $t_0$, the detection signal $E_k$ corresponding to the ultrasonic pulse transmitted through the housing 14 to the detector transducer 28 where it arrives at the point in time $t_k$, and the detection signal $E_2$ corresponding to the ultrasonic pulse transmitted through the interspace 20 to the detector transducer 28 when the interspace is filled with air and which arrives at detector transducer 28 at the point in time $t_2$. The existing detection pulse $E_2$ indicates that the level to be monitored has not been attained.

Plot B shows the corresponding pulses for the case in which the interspace 20 is filled with the bulk solid. In this case only the ultrasonic pulse transmitted through the housing 14 arrives at the detector transducer 28 for which the detection signal $E_k$ is output, whilst the detection signal $E_2$ is missing. The existing detection signal $E_k$ indicates that the system is working properly and the lack of the detection signal $E_2$ is an indication that the level to be monitored has been attained.

Plot C of FIG. 5 shows the control signals $C_k$ and $C_2$ applied to the control circuit 40 at the gating circuits 46 and 48 respectively. The control signal $C_k$ opens the gating circuit 46 during a time window $T_k$ in which the point in time $t_k$ is located. The control signal $C_2$ has the same effect as in the case of FIGS. 2 and 3, it opening the gating circuit 48 during a time window $T_2$ in which then, when the interspace 20 is filled with air the point in time $t_2$ of outputting the detection signal $E_2$ is located for all speeds of sound occurring in air.

Thus, when a detection signal $E_2$ arrives within the time window T2 it is passed on by the gating circuit 48 to the monoflop 58 resulting in the latter being switched to the working state or, if it was already in the working state, it is maintained in the working state by retriggering within its holding time. In this state the output signal of the monoflop 58 indicates that the interspace 20 is filled with air and thus the level to be monitored has not been attained. When, instead, no further detection signal $E_2$ arrives within the holding time, then the monoflop 58 is OFF at the end of the holding time and its output signal assumes the opposite state indicating that the interspace 20 is filled with the material and thus the level to be monitored has been attained or exceeded.

As long as the system operates faultlessly a detection signal $E_k$ is passed by the gating circuit 46 to the monoflop 56 within the time window $T_k$ in each emission cycle, as a result of which the monoflop 56 is continuously maintained in its working state in which its output signal indicates faultless operation. Should the detector transducer 28 fail to continue to output a detection signal $E_k$ due to a fault the monoflop 56 is OFF at the end of the holding time and its output signal indicates the existence of a fault condition. The monoflop 56 thus has the same function as the monoflop 54 as shown in FIG. 2.

Preferably the holding time of each of the monoflops 56 and 58 is a multiple of the emission pulse period to prevent a change in the level indication or a fault signal due to a sporadic lack of individual pulses.

Depending on the configuration of the support of the ultrasonic transducer 24 and 28 it is also possible that the path of the ultrasonic pulses through the support is so long that the detection signal $E_k$ does not arrive until after the detection signal $E_2$ transmitted through air. This is favorable since the detection signal $E_k$ serving fault-checking can be greatly expanded in time depending on the configuration of the device, one reason for this being, for example, multiple reflections resulting in noise signals also following the actual fault check signal formed by the first ultrasonic pulse detected via the support.

When the fault check signal arrives prior to the detection signal $E_2$ there is the possibility that these noise signals extend up to the portion of the time window $T_2$ and make analysis of the detection signal $E_2$ difficult or even sham a non-existent detection signal $E_2$ which would result in a fault indication. This can be prevented by configuring the support so that the transit time of the ultrasonic pulses transmitted by the support is so long that these always arrive at the detector transducer 28 after the ultrasonic pulses transmitted through the interspace 20. In the example embodiment illustrated in which the support is formed by the housing 14 this can be achieved, for example, by making the two housing sections 16 and 18 longer, whereby then, of course, the control circuit 40 needs to control the gating circuit 46 so that the time window $T_k$ is behind the time window $T_2$.

It is also possible to combine the two aforementioned embodiments in which the arrival of detection signals in all three time windows $T_1$, $T_2$ and $T_k$ is checked. The same assembly may then also be made use of without any modification for monitoring the level of liquids and bulk solids. It is particularly of advantage in this case to configure the support so that the fault check signal $E_k$ arrives at the detector transducer 28 not before the detection signal $E_2$ has been transmitted through the air because it is otherwise difficult to prevent the noise signals contained in the detection signal $E_k$ from extending into the portion of one of the time windows $T_1$ and $T_2$.

For the ultrasonic transducers 24 and 28 piezoelectric transducers are preferably used, it being known that a piezoelectric transducer consists of a disk of a piezocrystal on both sides of which metallizations are deposited which serve as electrodes. When an alternating voltage is applied to the electrodes the piezocrystal is caused to vibrate mechanically at the frequency of the alternating voltage and when mechanical vibrations are transmitted to the piezocrystal it generates between the electrodes an alternating voltage having the frequency of the mechanical vibrations. In the case of the sensor 10 as shown in FIG. 1 each electrode of transducer 24, 28 is connected to the metal wall of the housing 14 adjoining the interspace 20, this metal wall simultaneously serving as the ground terminal whilst the other electrode of the transducer 24 is connected via the lead 30 to the energizing circuit 32 and the other electrode of the transducer 28 via the lead 34 to the analyzer circuit 36.

When using conventional piezoelectric transducers in the sensor as described there is, however, the problem that that the dimensions of the transducers need to be larger the lower the operating frequency. This is why in accordance with a preferred embodiment of the invention piezoelectric transducers are employed consisting of a porous piezoelectric ceramic having the connectivity 3—3.

The term "connectivity" was introduced by R. E. Newnham to characterize the structures of multi-phase solids as also applied to composite electroceramics (R. E. Newnham "Composite Electroceramics, Ferroelectrics 1986, Vol. 86, pages 1–32). The connectivity designates the spatial directions in a three-dimensional right-angled system of coordinates in which the components of each phase are fully connected to each other, 0 meaning that the components of each phase are fully connected to each other in no spatial direction, 1 that the components of each phase are fully connected to each other in only one spatial direction, and so on. Thus "connectivity 3—3" means that in the case of a two-phase solid the components of each of the two phases are fully connected to each other in all three spatial directions.

In the paper "Dielectric, elastic and piezoelectric properties of porous PZT ceramics" by W. Wersing, K. Lubitz and J Mohaupt in Ferroelectrics 1986, Vol. 68, pages 77–97 the term connectivity is also applied to porous ceramics which are viewed as being two-phase solids in which the one phase is formed by the ceramic material and the other phase by the pores. Thus, in the case of a porous ceramic having the connectivity 3—3 both the ceramic material and the pores are fully connected to each other in all three spatial directions.

Such piezoelectric transducers of a porous piezoelectric ceramic having the connectivity 3—3 can operate with relatively small dimensions in the low-frequency ultrasonic range between approximately 100 and 300 kHz and are thus especially well suited for use in the assembly as described above, A further advantage of such piezoelectric transducers is that their acoustic impedance is of the order of magnitude of that of the material of the sensor housing so that they can be employed without an adapter film.

It will be appreciated that that said in the above description as regards the transmission of ultrasonic waves in air applies just as well to the transmission of ultrasonic waves in other gases. Accordingly, the method as described may be put to use without any change also for monitoring the level in a container, the interspace of which contains a gas other than air.

What is claimed is:

1. A method for monitoring a predetermined level of a material in a container with the aid of two ultrasonic transducers mounted in line with the level to be monitored on the container such that an interspace exists between the ultrasonic transducers into which the material enters on attaining the level to be monitored, whereby the one ultrasonic transducer is an emitter transducer energized at predetermined points in time to emit ultrasonic pulses into the interspace whilst the other ultrasonic transducer is a detector transducer which detects the ultrasonic pulses during a first time window corresponding to the transit time of said ultrasonic pulses from said emitter transducer to said detector transducer in air and converts the detected ultrasonic pulses into electrical detection signals, the analysis of which indicates whether material is in the interspace between the ultrasonic transducers wherein said emitter transducer emitting said ultrasonic pulses is energized at a frequency which is so low that said ultrasonic pulses are transmitted through said interspace to said detector transducer even when said interspace is filled with air and it is determined whether said detector transducer outputs a detection signal during the first time window.

2. The method as set forth in claim 1 wherein said frequency of said ultrasonic pulses is smaller than 300 kHz.

3. The method as set forth in claim 2 wherein said frequency of said ultrasonic pulses is in the range 100 to 300 kHz.

4. The method as set forth in claim 1 for monitoring a predetermined level of a liquid in said container wherein it is determined whether said detector transducer outputs a detection signal during a second time window corresponding to the transit time of said ultrasonic pulses from said emitter transducer to said detector transducer in said liquid.

5. The method as set forth in claim 1 wherein said emitter transducer and said detector transducer are mounted on a common support and wherein it is determined whether said detector transducer outputs a detection signal during a second time window corresponding to the transit time of said ultrasonic pulses from said emitter transducer to said detector transducer via said support of said two transducers.

6. An assembly for monitoring a predetermined level of a material in a container comprising two ultrasonic transducers mounted on said container in line with the predetermined level to be monitored, such that an interspace exists between said ultrasonic transducers into which said material enters on attaining the predetermined level to be monitored, the one ultrasonic transducer being an emitter transducer configured and arranged so that on being energized by an electrical alternating voltage pulse it emits ultrasonic pulses into said interspace whilst the other ultrasonic transducer is a detector transducer configured and arranged so that it converts said detected ultrasonic pulses into electrical detection signals, including an energizing circuit to energize said emitter transducer at predetermined points in time of emission to emit ultrasonic pulses, and an analyzer circuit for analyzing said electrical detection signals furnished by said detector transducer to determine whether or not said interspace is filled with said material to be monitored wherein said energizing circuit energizes said emitter transducer for emitting ultrasonic pulses at a frequency which is so low that said ultrasonic pulses are transmitted through said interspace to said detector transducer even when said interspace is filled with air and said analyzer circuit contains a means to distinguish whether said detector transducer outputs a detection signal during a first time window corresponding to the transit time of said ultrasonic pulses from said emitter transducer to said detector transducer in air.

7. The assembly as set forth in claim 6 for monitoring a predetermined level of a liquid in said container wherein said analyzer circuit comprises means for determining whether said detector transducer outputs a detection signal during the a second time window corresponding to the transit time of said ultrasonic pulses from said emitter transducer to said detector transducer in said liquid.

8. The assembly as set forth in claim 6 wherein said emitter transducer and said detector transducer are mounted on a common support and wherein said analyzer circuit comprises a means for determining whether said detector transducer outputs a detection signal during a second time window corresponding to the transit time of said ultrasonic pulses from said emitter transducer to said detector transducer via said support of said two ultrasonic transducers.

9. The assembly as set forth in claim 8 wherein said support of said two ultrasonic transducers is configured so that the transit time of said ultrasonic pulses from said emitter transducer to said detector transducer via said support is longer than that in air.

10. The assembly as set forth in claim 6 wherein said two ultrasonic transducers are piezoelectric transducers made of a porous piezoelectric ceramic having the connectivity 3—3.

11. The method as set forth in claim 2 for monitoring a predetermined level of a liquid in said container wherein it is determined whether said detector transducer outputs a detection signal during a second time window corresponding to the transit time of said ultrasonic pulses from said emitter transducer to said detector transducer in said liquid.

12. The method as set forth in claim 3 for monitoring a predetermined level of a liquid in said container wherein it is determined whether said detector transducer outputs a detection signal during a second time window corresponding to the transit time of said ultrasonic pulses from said emitter transducer to said detector transducer in said liquid.

13. The method as set forth in claim 2 wherein said emitter transducer and said detector transducer are mounted on a common support and wherein it is determined whether said detector transducer outputs a detection signal during a second time window corresponding to said transit time of said ultrasonic pulses from said emitter transducer to said detector transducer via said support of said two transducers.

14. The method as set forth in claim 3 wherein said emitter transducer and said detector transducer are mounted on a common support and wherein it is determined whether said detector transducer outputs a detection signal during a second time window corresponding to said transit time of said ultrasonic pulses from said emitter transducer to said detector transducer via said support of said two transducers.

15. The method as set forth in claim 4 wherein said emitter transducer and said detector transducer are mounted on a common support and wherein it is determined whether said detector transducer outputs a detection signal during a third time window corresponding to said transit time of said ultrasonic pulses from said emitter transducer to said detector transducer via said support of said two transducers.

16. The assembly as set forth in claim 7 wherein said emitter transducer and said detector transducer are mounted on a common support and wherein said analyzer circuit comprises a means for determining whether said detector transducer outputs a detection signal during a third time window corresponding to the transit time of said ultrasonic pulses from said emitter transducer to said detector transducer via said support of said two ultrasonic transducers.

17. The assembly as set forth in claim 7 wherein said two ultrasonic transducers are piezoelectric transducers made of a porous piezoelectric ceramic having the connectivity 3—3.

18. The assembly as set forth in claim 8 wherein said two ultrasonic transducers are piezoelectric transducers made of a porous piezoelectric ceramic having the connectivity 3—3.

19. The assembly as set forth in claim 9 wherein said two ultrasonic transducers are piezoelectric transducers made of a porous piezoelectric ceramic having the connectivity 3—3.

20. The method as set forth in claim 11 wherein said emitter transducer and said detector transducer are mounted on a common support and wherein it is determined whether said detector transducer outputs a detection signal during a third time window corresponding to the transit time of said ultrasonic pulses from said emitter transducer to said detector transducer via said support of said two transducers.

21. The method as set forth in claim 12 wherein said emitter transducer and said detector transducer are mounted on a common support and wherein it is determined whether said detector transducer outputs a detection signal during a third time window corresponding to the transit time of said ultrasonic pulses from said emitter transducer to said detector transducer via said support of said two transducers.

22. An apparatus for monitoring the presence of a material in an interspace, the apparatus comprising:
   a first transducer;
   a second transducer proximate to the first transducer, the first and second transducers defining the interspace;
   an energizing circuit coupled to the first transducer, the energizing circuit configured to energize the first transducer to emit a pulse into the interspace;
   an analyzing circuit coupled to the second transducer, the analyzer circuit configured to monitor the second transducer for reception of the pulse during a first time window corresponding to a transit time of the pulse in the interspace when the interspace is filled with air, the analysis of which indicates whether material is in the interspace.

23. The apparatus of claim 22, wherein the analyzer is further configured to associate reception of the pulse during the first time window with the presence of air in the interspace.

24. The apparatus of claim 23, wherein the analyzing circuit is further configured to monitor the second transducer for reception of the pulse during a second time window corresponding to a transit time of the pulse in the interspace when the interspace is filled with liquid, and further configured to associate reception of the pulse during the second time window with the presence of liquid in the interspace.

25. The apparatus of claim 23, further comprising a common support wherein the first and second transducers are mounted, and wherein the analyzing circuit is further configured to monitor the second transducer for reception of the pulse during a second time window corresponding to a transit time of the pulse through the common support.

26. The apparatus of claim 25, wherein the analyzing circuit is further configured to monitor the second transducer for reception of the pulse during a third time window corresponding to a transit time of the pulse in the interspace when the interspace is filled with liquid, and further configured to associate reception of the pulse during the second time window with the presence of liquid in the interspace.

27. The apparatus of claim 23, wherein the analyzer circuit is further configured to associate a failure to receive the pulse during the first time window to the presence of a material in the interspace.

* * * * *